(12) United States Patent
Kullenberg et al.

(10) Patent No.: US 10,197,513 B2
(45) Date of Patent: Feb. 5, 2019

(54) METHOD AND APPARATUS FOR ESTIMATION OF HEAT VALUE USING DUAL ENERGY X-RAY TRANSMISSION AND FLUORESCENCE MEASUREMENTS

(71) Applicant: MANTEX AB, Kista (SE)

(72) Inventors: Ragnar Kullenberg, Oskarstrom (SE); Ralf Torgrip, Alvsjo (SE)

(73) Assignee: MANTEX IP AB, Kista (SE)

( * ) Notice: Subject to any disclaimer, the term of this patent is extended or adjusted under 35 U.S.C. 154(b) by 257 days.

(21) Appl. No.: 15/028,656

(22) PCT Filed: Oct. 11, 2013

(86) PCT No.: PCT/EP2013/071306
§ 371 (c)(1),
(2) Date: Apr. 11, 2016

(87) PCT Pub. No.: WO2015/051853
PCT Pub. Date: Apr. 16, 2015

(65) Prior Publication Data
US 2016/0258891 A1    Sep. 8, 2016

(51) Int. Cl.
*G01N 23/087* (2018.01)
*G01N 23/223* (2006.01)
(Continued)

(52) U.S. Cl.
CPC ....... *G01N 23/2206* (2013.01); *G01N 23/087* (2013.01); *G01N 23/223* (2013.01);
(Continued)

(58) Field of Classification Search
CPC ........ G01N 23/00; G01N 23/02; G01N 23/06; G01N 23/08; G01N 23/087; G01N 23/22;
(Continued)

(56) References Cited

U.S. PATENT DOCUMENTS

| 3,934,139 A | 1/1976 | Ohata et al. |
| 6,130,931 A | 10/2000 | Laurila et al. |

(Continued)

FOREIGN PATENT DOCUMENTS

| CN | 2809646 Y | 8/2006 |
| CN | 102884422 A | 1/2013 |

(Continued)

OTHER PUBLICATIONS

International Search Report (PCT/ISA/210) dated Jun. 12, 2014, by the European Patent Office as the International Searching Authority for International Application No. PCT/EP2013/071306.

(Continued)

*Primary Examiner* — Anastasia Midkiff
(74) *Attorney, Agent, or Firm* — Buchanan Ingersoll & Rooney P.C.

(57) ABSTRACT

A method and apparatus for estimating a heating value of a biological material. The method includes irradiating of the biological material with X-ray radiation of at least two different energy levels, measuring of an amount of radiation transmitted through the biological material at these energy levels, and measuring fluorescent radiation emitted by the biological material when irradiated at these energy levels. A final estimate of the heating value is then determined based on a preliminary estimate of the heating value of the biological material based on the measured transmitted radiation and a correction value based on the fluorescent radiation.

19 Claims, 3 Drawing Sheets

(51) Int. Cl.
*G01N 33/46* (2006.01)
*G01N 23/2206* (2018.01)
*G01N 33/22* (2006.01)

(52) U.S. Cl.
CPC ............. *G01N 33/46* (2013.01); *G01N 33/22* (2013.01); *G01N 33/222* (2013.01); *G01N 2223/045* (2013.01); *G01N 2223/071* (2013.01); *G01N 2223/619* (2013.01)

(58) Field of Classification Search
CPC .. G01N 23/2206; G01N 23/223; G01N 33/00; G01N 33/22; G01N 33/222; G01N 33/46; G01N 2223/00; G01N 2223/03; G01N 2223/04; G01N 2223/045; G01N 2223/05; G01N 2223/07; G01N 2223/071; G01N 2223/076; G01N 2223/0766; G01N 2223/619; G01N 2223/643; G01T 1/00; G01T 1/16; G01T 1/1603; G01T 1/24; G01T 1/28
See application file for complete search history.

(56) References Cited

U.S. PATENT DOCUMENTS

| | | | |
|---|---|---|---|
| 6,421,415 B1* | 7/2002 | Peczkis | G01N 23/2206 378/45 |
| 7,690,268 B2 | 4/2010 | Wolfschaffner | |
| 2001/0014136 A1 | 8/2001 | Jans et al. | |
| 2011/0044426 A1* | 2/2011 | Ullberg | G01N 23/223 378/45 |
| 2011/0176658 A1* | 7/2011 | Ullberg | G01N 33/46 378/53 |
| 2011/0235777 A1 | 9/2011 | Gozani et al. | |
| 2013/0003925 A1 | 1/2013 | Oden et al. | |
| 2013/0079918 A1* | 3/2013 | Spencer | B07C 5/3416 700/223 |
| 2013/0141115 A1 | 6/2013 | Bourely et al. | |
| 2013/0195243 A1* | 8/2013 | Oden | G01N 23/087 378/53 |
| 2014/0226694 A1 | 8/2014 | Kullenberg et al. | |

FOREIGN PATENT DOCUMENTS

| | | |
|---|---|---|
| CN | 202 854 070 U | 4/2013 |
| EP | 0 718 553 A1 | 6/1996 |
| EP | 2543997 A1 | 1/2013 |
| EP | 2 602 030 A1 | 6/2013 |
| GB | 2 122 741 A | 1/1984 |
| JP | 2001183315 A | 7/2001 |
| WO | WO 00/16078 A1 | 3/2000 |
| WO | WO 2013/004593 A1 | 1/2013 |

OTHER PUBLICATIONS

LC Morais et al., "Trace elements and heating value from sewage sludge, Barueri, Sao Paulo, Brazil", International Journal of Environmental Studies, Jan. 1, 2006, pp. 331-336, vol. 63.
Office Action (The First Office Action) dated Mar. 2, 2018, by the State Intellectual Property Office of the People's Republic of China in corresponding Chinese Patent Application No. 201380080088.6, and a partial English Translation of the Office Action. (15 pages).
Chinese Agents Report dated Mar. 26, 2018. (3 Pages).

* cited by examiner

METHOD AND APPARATUS FOR ESTIMATION OF HEAT VALUE USING DUAL ENERGY X-RAY TRANSMISSION AND FLUORESCENCE MEASUREMENTS

TECHNICAL FIELD OF THE INVENTION

The present invention relates to a method and an apparatus for estimation of the heat value of a biological material in an automated procedure. The invention is particularly useful for measuring the heating value of biofuels, such as wood chips and coal.

BACKGROUND

Biological materials, and in particular biomass fuels, are commonly burnt in processes for generation of heat and energy. One of the most important biomass fuels is wood. However, different biomass fuels generate different amounts of heat and different amounts and types of residuals after burning. Great deviations exist also for different types and qualities of wood. This makes it difficult to control a burning or combustion process effectively.

Thus, it is often of great importance to be able to estimate the heating value of a biological material. For example in bio-energy systems, including burning systems, it is of great importance to estimate the heating value of the material fed to the bio-energy system, in order to control the burning process more precisely, and improve its efficiency. The heating value typically varies between different types of biological materials, but also within each type. For example, the same type of biological material may have different moisture content, different ash properties, etc. For example in wood, this may depend on a variety of factors including the type of tree or shrub, the part of the tree or shrub (bark, wood, leaves), etc.

Many suggestions have been proposed during the years to provide estimates of heating value of different materials. For example, U.S. Pat. No. 7,690,268 discloses a method for determining heating value of a flowing material. However, this method can only be used on a single, predetermined material, for which the calorific values are known beforehand. Thus, this method cannot be used when many different materials are used simultaneously. Similarly, the method disclosed in U.S. Pat. No. 3,934,139 is also related to estimation of heating value for one specific material, and also requires determination of the density of the material. The method disclosed in EP 0 718 553 determines the moisture content of a material, and assumes that this is correlated to the heating value. Even though this assumption may be correct for some materials, it is not generally valid, which makes the method difficult to use for systems handling a variety of biological materials. Further, common problems with such known methods are that that the apparatuses are large and expensive, that the methods are relatively tedious and cumbersome to perform, and/or that the results are imprecise and unreliable.

In WO 13/004593 by the same applicant, a much improved method was presented, where an estimate of the heating value was obtainable directly from transmission measurements obtained when irradiating the sample at two different energy levels of e.g. X-ray, and correlating this with reference data obtained through e.g. adiabatic bomb calorimeter measurement. However, sometimes there is a relatively large content of non-combustible elements in the biological material, such as calcium, potassium and silica, e.g. in the form of oxides and/or carbonates, magnesium, phosphor, and heavy metals, such as cadmium, zinc and copper. The content of such non-combustible elements may also vary significantly over time, and from sample to sample. In such cases, it may be difficult to use this previously known method for determination of heating values efficiently and accurately.

There is therefore a need for an improved method for a fast and reliable estimation of the heating value of a biological material, and in particular a method which can be used also when handling a variety of biological materials, and with variable content of non-combustible elements.

SUMMARY OF THE INVENTION

It is therefore an object of the present invention to provide an improved method and apparatus for estimating the heating value of a biological material, preferably in an automated process, which overcome or at least alleviate the above-discussed problems of the prior art.

This object is achieved by means of the invention as defined in the appended claims.

According to a first aspect of the invention there is provided a method for estimating a heating value of a biological material, comprising:

irradiating the biological material with X-ray radiation of at least two different energy levels;

measuring an amount of radiation transmitted through said biological material at said energy levels;

measuring fluorescent radiation emitted by the biological material when irradiated at said energy levels;

determining a final estimate of the heating value based on a preliminary estimate of the heating value of said biological material based on said measured transmitted radiation and a correction value based on said fluorescent radiation.

The present invention is based on the realization that the previously known method, as disclosed in WO 13/004593 by the same applicant, and which is hereby incorporated in its entirety by reference, can be significantly improved by also measuring fluorescence radiation from the sample, and use this as a correction. The fluorescence radiation (XRF) is preferably measured simultaneously with the transmission radiation (DXA).

Measurement of transmission radiation is a very powerful technique, since it is based on the absorption of the sample, and completely penetrates and pictures the sample material. Since the DXA here uses at least two different radiation energies, it is possible to quantify different elements of the sample, since different elements have different X-ray absorption at different energies. However, additional elements, and in particular elements having a relatively high atomic number, such as an atomic number exceeding 10, provides a source of error, in particular if the content of such elements varies. With this DXA measurement, the transmission values may be correlated directly to the heating value, without the need to determine the type of biological material used, the moisture content, etc.

Fluorescence measurements (XRF) are per se known, and energy dispersive XRF may e.g. be used to determine the quantity of X-ray being emitted by fluorescence from the irradiated sample. Each element exhibit unique energies in the emitted fluorescence photons, and therefore provides information about which elements that are present in the sample, and the quantity of these elements.

However, a drawback with XRF is that elements having a low atomic number, typically 10 or less, are difficult to measure and quantify. This means that XRF can typically not be used to measure the most important constituents in biological materials and biofuels, such as oxygen (Z=8), and carbon (Z=6). Further, XRF primarily measures the surface of a material, since XRF quanta from atoms with low Z are prone to self-attenuation in the sample and attenuation by ambient air.

However, the present invention makes use of the different possibilities of these two techniques in a remarkably efficient way. By using DXA to measure combustible elements having lower atomic number, such as carbon and water, and to use XRF to determine non-combustible elements, a remarkably accurate estimate of heating value can be obtained, even when the properties of the biological material to be measured varies significantly. The DXA measurement may consequently be used to determine a preliminary heating value, whereas the XRF is used to provide a correction value, by which the preliminary heating value may be adjusted to a more correct final estimate of the heating value.

Notably, an exact determination of the constituents and quantity of individual elements is not necessary, since the correction value based on the XRF measurement can instead be used by calibration, i.e. correlation to reference measurements, and by looking at integrated values over certain energy bands. Thus, XRF is here used differently than in conventional XRF measurements, where individual peaks are analyzed, to determine and quantify the constituents. Thus, a total influence from non-combustible elements, such as calcium (Z=20), potassium (Z=19) and silicon (Z=14), and possibly also magnesium, phosphor, and heavy metals, such as cadmium, zinc and copper, can be analyzed, and used to provide a correction value to improve the preliminary heating value estimate.

Further, since the DXA and XRF measurements can be made simultaneously, and all in a very short time, e.g. in a few milliseconds, it is possible to use this method in on-line systems, e.g. where biological material is transported on a conveyor belt or similar, and to provide real-time control of the subsequent process(es).

The term "heating value" is here used to indicate the net obtainable energy produced by combustion, in joules or kcal, for a unit mass of the biological material. Heating value may also be referred to as calorific value. The method of the present invention may be used either to estimate the gross calorific value, commonly referred to as the high heating value, or the net calorific value, commonly referred to as the low heating value. The difference between the two is that the net calorific value does not include the energy needed to vaporize the water in the biological material.

The present invention is particularly useful for estimating the heating value in wood chips, but it may also be used for other forms of wood, as well as for other types of biological material, such other types of biomass fuel, forest residues, coal, etc. The invention is particularly useful for biological material in a liquid or separated form, and preferably in the form of chips. However, the invention is also useable for other types of biological material.

By different energies or different energy levels is in the context of the present application meant a difference in mean energies. Thus, radiation of a certain energy, as used in the present application, refers to radiation having a mean energy at this level, even though the radiation may be distributed within a range of different energies. Further, the X-ray source(s) may be polychromatic. Consequently, radiation of different energies or energy levels may even be fully or partially overlapping in energy ranges, as long as the mean energies are different from each other.

The method of the present invention makes use of irradiation of two or more different energy levels, and determines the heating value of the material, directly or indirectly, from the measured transmission energy, i.e. the amount of the radiation of each energy that is absorbed in the material. Different material types, such as different sort of wood, have different absorption coefficients. However, the inventive system compensates for this in a very effective way by e.g. using the correlation to the heating values for the reference materials obtained by calorimeter measurements, and by adding a correction based on non-combustible elements contained in the biological material. This correction is obtained through the above-discussed XRF measurements.

The method/apparatus according to the present invention is very well suited for use in in-line measurements of conveyor lines where material is transported, in pipe-lines, etc. This is possible, since e.g. the present invention can be used for various and varying heights and forms of the biological material. However, it is also very useable for measuring samples of material arranged in sample containers, e.g. for sample testing in process industries, in the field measurements, etc. The present invention may be used in fully or partly automated procedures, and requires no, or very limited, operator interaction.

The preliminary estimate of the heating value is preferably based on the measured transmitted radiation in correlation with correlation values obtained by radiation transmitted through a number of different reference materials with known heating values. The reference measurements to obtain the correlation is preferably assembled by measuring transmission of X-ray radiation of at least two different energy levels through a plurality of different material types, and by measuring the heating value of said materials by means of a conventional method. The material types may e.g. be different sorts of wood, such as birch, spruce, pine, oak, and alder, and also coal and other biofuels. The correlation only needs to be established during the initialization, and can then be reused repeatedly. Consequently, there is no particular need for speedy processes during these reference measurements.

The heating values for these reference materials are preferably obtained by calorimeter measurements, and most preferably by an adiabatic bomb calorimeter measurement made in accordance with international standard ISO 1928: 1995.

Due to the efficient estimation of the heating value, it is possible to control the burning/combustion process in relation to the heating value, in order to obtain a more effective burning/combustion.

The present invention may be used in fully or partly automated procedures, and requires no, or very limited, operator interaction. The sending of information related to the heating value to a control system and the use of said information for the control of the subsequent process may also be automated. When used in an on-line system, the subsequent process can hereby be controlled in real-time based on said information. However, it is also possible to store the information for later use in association with the specific sample or batch of biological material.

The fluorescent radiation is preferably used to determine the amount of at least one element having an atomic number exceeding 10 in the biological sample, and to determine a correction value based on this.

The determination of the final estimated heating value preferably comprises the step of subtracting the correlation value from the preliminary estimate of the heating value.

The correction value is preferably estimated by integration of at least one energy band in the fluorescent radiation spectrum. The spectrum integration may e.g. be made in at least one energy band comprising or being a sub-range of 1.5-10 keV and/or 25-90 keV. Further, the energy band used for spectrum integration preferably has an extension of at least 5 keV, and most preferably at least 7 keV. Additionally or alternatively, the spectrum integration can be made over at least one energy corresponding to a spectrum peak characteristic of at least one of a heavy metal, calcium, potassium, silicon, magnesium and phosphorus. The correction value may be estimated as an addition of weighted spectrum integrations over specific energies or bands of energies of the fluorescence spectrum.

The at least one spectrum integration is preferably correlated to a corresponding reduction in heating value by means of measurements of known reference materials.

The determination of the preliminary estimate of the heating value preferably comprises the steps of:

determining a quotient between transmission estimates based on said transmission values of two of said at least two energy levels, for each combination of said at least two energy levels;

multiplying each quotient with a coefficient for each quotient; and adding said quotients multiplied by said coefficients, wherein said coefficients are determined by said correlation.

Thus, the preliminary estimate of the heating value may be calculated based on the quotient between two or more measurements of different energy levels, as:

$$W=a*K1+b*K2+c*K3+\ldots$$

K is here the quotient between measurements at different energy levels. Hereby, if two energy levels are used, one K is obtained. If three energy levels are used, three K:s are obtained. If four energy levels are used, six K:s are obtained, etc. If three energy levels are used, the three K:s would be: K1=R1/R2, K2=R2/R3 and K3=R1/R3.

Thus, for only two energy levels, the heating value may be estimated as $W=a*K1$, and if three energy levels are used, as $W=a*K1+b*K2+c*K3$, and if four energy levels are used, as $W=a*K1+b*K2+c*K3+d*K4+e*K5+f*K6$.

The coefficients, denominated a-f above, are determined in the above-discussed correlation, based on the reference measurements. The correlation between heating value and the transmission values is surprisingly good even if only two energy levels are used, but may be improved even further if three or more energy levels are used.

In the transmission estimates, said quotients are preferably logarithmic quotients of a calibrated reference values for the transmission at the energy level and the transmission values through the biological material at the same energy level. The quotients between said transmission estimates are preferably K-values, said K-values being calculated as:

$$K_{AB} = \frac{\ln(N_{0A}/N_A)}{\ln(N_{0B}/N_B)}$$

wherein $N_{0A}$, $N_{0B}$ are the calibrated reference values for the transmission at the two energy levels A and B, and $N_A$, $N_B$ are the transmission values through the biological material at said energy levels.

It has been found that the correlation between the K-value(s) and the heating value(s) is relatively linear for many types of biological material, in particular for many sorts of wood, and accordingly, relatively few specific values from the reference measurements can still be used to provide accurate estimations of a broad range of heating values in the sample material.

The amount of radiation transmitted through the sample of the biological material at the two energy levels is preferably determined in relation to a calibration reference value. The calibration reference value can e.g. be determined by measurement of the transmission of radiation through a reference material of a predetermined thickness, which is preferably made immediately before and/or after the each measurement through the biological material, the reference material e.g. being aluminum. Hereby, it is ensured that adequate calibration is always at hand.

The biological material is preferably transported on a conveyor line, wherein the biological material is irradiated with X-ray radiation of at least two different energy levels in a plane substantially perpendicular to a direction of advancement of said conveyor line. Hereby, the amount of radiation transmitted through said biological material at said two energy levels is preferably determined for a plurality of radiation paths penetrating said biological material in the plane substantially perpendicular to the direction of advancement of said conveyor line.

The radiation of said two or more energy levels may be emitted from a single radiation source, or from two or more separate radiation sources. The radiation source(s) preferably operate(s) in the energy range 20-150 kVp. Here, kVp (Peak kilovoltage) denotes the maximum voltage applied across an X-ray tube. It determines the kinetic energy of the electrons accelerated in the X-ray tube and the peak energy of the X-ray emission spectrum. The actual voltage across the tube may fluctuate.

The irradiation of the sample of the biological material with electromagnetic radiation of at least two different energy levels preferably comprises a first irradiation with a first energy level, and a subsequent second irradiation with a second energy level. Alternatively, the radiation source may comprise two or several separate juxtaposed radiation tubes which radiate either simultaneously or sequentially. Preferably, the radiation of different energies traverses the material to be measured along essentially the same path.

According to a second aspect of the invention, there is provided an apparatus for estimating a heating value of a biological material, comprising:

a radiation source for irradiation of a biological material with X-ray radiation of at least two different energy levels;

a detector for receiving X-ray radiation transmitted through said biological material, for determination, for each energy level, the amount of radiation transmitted through the biological material;

a fluorescence detector for measuring fluorescent radiation emitted by the biological material when irradiated at said energy levels;

a controller arranged to determine a final estimate of the heating value based on a preliminary estimate of the heating value of said biological material based on said measured transmitted radiation and a correction value based on said fluorescent radiation.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIG. 2a-b schematically illustrates an embodiment of the invention where the material to be measured is arranged in a sample container, wherein

DETAILED DESCRIPTION OF PREFERRED EMBODIMENTS

Figure 1:
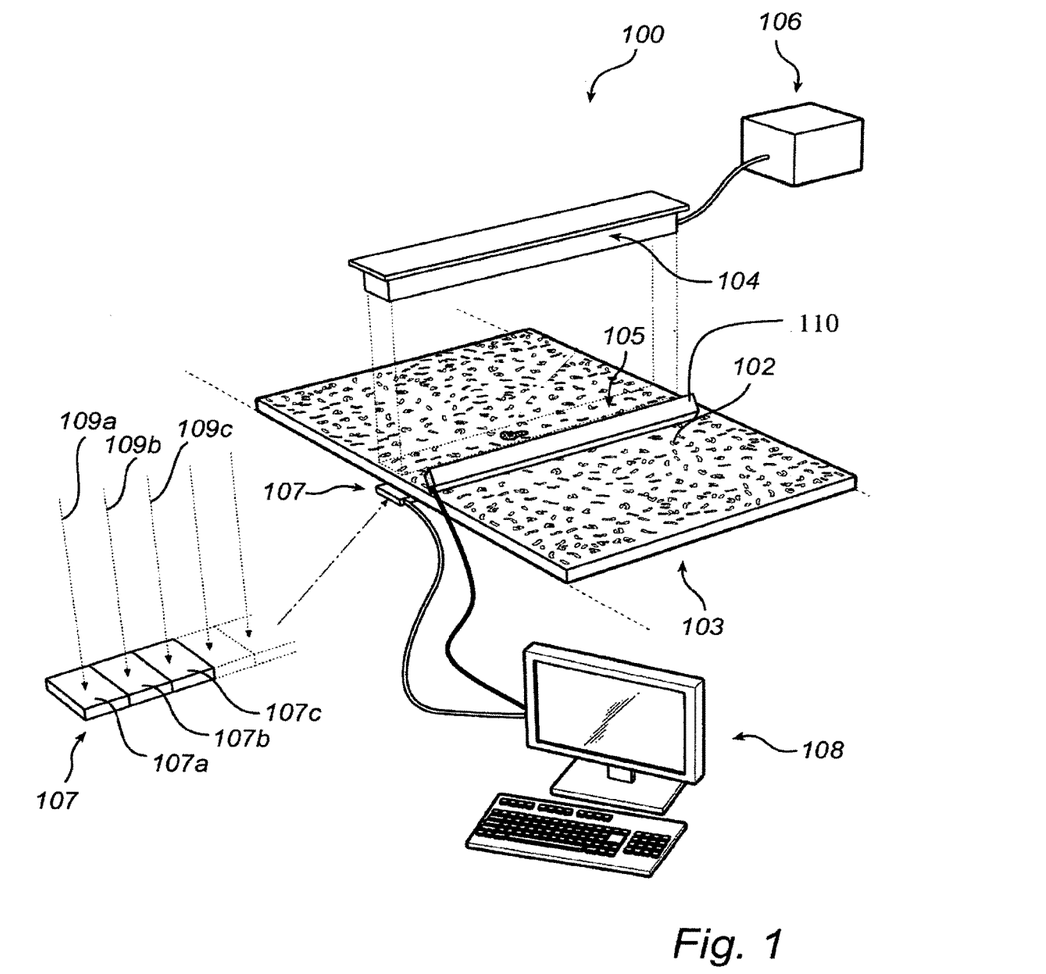
FIG. 1 schematically illustrates a measurement device for estimating a heating value in a biological material transported on a conveyor line.

FIG. 1 schematically illustrates an embodiment of a measurement device 100 for estimating a heating value of a biological material 102 transported on a conveyor line 103. The biological material 102 may typically be wood chips, or other biomass fuels.

If the height and properties of the material varies, it is preferred to scan essentially all of the material moved past the measurement device. If there is no significant variation in height and material properties over time, it may suffice to measure in a single point or target area.

In order to scan essentially all of the material, the measurement device comprises a radiation source 104 adapted to irradiate a target area 105 that spans across the width of the conveyor line. The radiation source 104 is adapted to provide radiation of at least two different energy levels/wavelengths. Preferably, the radiation source is an X-ray tube for provision of X-ray radiation of two or more different energies. Preferably, the X-ray tube operates in the range 20-150 kVp. The output radiation from the radiation source is preferably directed towards the target area through a collimator and a lens (not shown). The radiation source 104 is controlled by means of a controller 106.

Alternatively, the radiation source 104 may comprise two or several separate juxtaposed radiation tubes, wherein the juxtaposed radiation sources radiate the different energies either simultaneously or sequentially. However, preferably the radiation having different energies traverses the material to be measured along essentially the same path. When radiation of two (or more) energies is emitted simultaneously from the radiation source the intensity of the two signals should preferably be measured individually. This may be implemented directly by making provisions such that certain portions of the detector by filtration only measure radiation having a certain energy level while others measure other energy levels. It may also be implemented by subsequent treatment of signals, allowing superimposed signals to be separated.

On the opposite side of the target area 105, a transmission detector 107 is arranged to receive radiation transmitted through material located in the target area 105. The detector is preferably a semiconductor detector comprising a linear array of semiconductor detector areas 107a-c distributed across the width of the conveyor line. The number of detector areas may vary due to the expected variations of ash content in the material, etc. The detector 107 is connected to a control unit 108 with a processor, e.g. an ordinary personal computer. The control unit receives detection data from the detector through a suitable interface, such as through a USB port.

On the side of the target area 105, a fluorescence detector 110 is arranged to receive fluorescence radiation emitted by the radiated material located in the target area 105. This detector may also be a semiconductor detector comprising a linear array of semiconductor detector areas distributed across the width of the conveyor line. The number of detector areas may vary due to the expected variations of ash content in the material, etc. The detector 110 is also connected to the control unit 108, and data from the detector may be received through a suitable interface. The fluorescence detector may also be situated in other positions than the one shown in the illustrated example, as long as the detector is outside the direct radiation path of the radiation emitted by the X-ray source.

In operation, the radiation source 104 irradiates the material in the target area 105 with electromagnetic radiation of at least two different energy levels. This may be achieved by sequentially irradiating the material with radiation of a first energy, and radiation of a second energy, i.e. the radiation source initially emits rays having one energy and then, by altering the voltage across the radiation tube, a different energy.

For each energy level, the amount of radiation transmitted through the material located in the target area 105 is measured on the opposite side of the target area 105 by the transmission detector areas 107a-c of the transmission detector, wherein each detector area 107a-c receives radiation that has penetrated the material 102 along a different radiation path 109a-c. Simultaneously, the fluorescence detector 110 measures the fluorescence radiation emitted by the material due to this irradiation.

In order to get a reference value for calibration, it is preferred to measure a calibration material. This can be achieved, for example, by measuring without any biological material present. Thus, in this case, a calibration measurement is obtained with air as a calibration material. Alternatively, the biological material may be replaced with a calibration material with known properties, such as aluminum. The calibration measurements may be obtained before measuring of the biological material, during initialization, or repeatedly during the process. Alternatively, calibration measurements may be obtained by letting the radiation source 104 and the detectors 107 and 110 measure an empty conveyor line such that the radiation passes through air and belt only on its way from the radiation source to the detector. It is also possible to use additional radiation sources and detectors situated on one or both sides of the conveyor belt.

Based on these calibration measurements, calibration values for the transmitted radiation are determined as:

$$N_{01,02} = N_{Air1,2} \exp(\mu x)$$

where $N_{01}$ and $N_{02}$ are the calibration values for energy level 1 and 2, respectively, $N_{Air1}$ and $N_{Air2}$ are the detected transmission values after passage through the known distance of air, $\mu$ is the known attenuation coefficient for air (cm$^{-1}$) and x is the known distance of air (cm) that separates the radiation source and the detector.

A K-value for the material is determined for the radiation received by each detector area 107a-c. The K-value is calculated as:

$$K = \frac{\ln(N_{01}/N_1)}{\ln(N_{02}/N_2)}$$

wherein $N_{01}$, $N_{02}$ are the calibrated reference values for the transmission at the two energy levels and $N_1$, $N_2$ are the transmission values through the biological material at the energy levels.

A correlation between heating values and the amount of radiation transmitted through the biological material is then determined. This is determined based on reference measurements of a number of different reference materials.

The reference measurements are preferably made with a calorimeter measurement of standard type, and preferably an adiabatic bomb calorimeter measurement is used. Most preferably, the adiabatic bomb calorimeter measurement is made in accordance with international standard ISO 1928: 1995.

The correlation between the heating values of the reference measurements and the transmission values is preferably made by correlation to the above-discussed K-values. Preferably, the heating value is calculated based on the quotient between two or more measurements of different energy levels, as:

$$W_{prel} = a_1*K1 + b_1*K2 + c_1*K3 + \ldots$$

where K is the quotients between each and every combination of measurements at different energy levels. Hereby, if two energy levels are used, one K is obtained. If three energy levels are used, three K:s are obtained. If four energy levels are used, six K:s are obtained, etc. If three energy levels are used, the three K:s would be: K1=R1R2, K2=R2/R3 and K3=R1/R3. Thus, for only two energy levels, the heating value may be estimated as W=a*K1, and if three energy levels are used, as $W_{prel}=a_1*K1+b_1*K2+c_1*K3$, and if four energy levels are used, as $W_{prel}=a_1*K1+b_1*K2+c_1*K3+d_1*K4+e_1*K5+f_1*K6$. The coefficients, denominated $a_1$-$f_1$ above, are determined and optimized mathematically to provide a correlation between the reference measurements and the heat energy as estimated based on the transmission measurements. Thus, the K-values may be used in a linear or polynomial representation of the correspondence between the K-value and the heating value, and this function may then be used for an estimate of the heating value based on the measured and calculated K-values of the sample material.

The correction value is further calculated, based on the detected fluorescence radiation. This may e.g. be correlated to previously measured reference materials with known heating values, in a similar way as in respect of the transmission radiation.

The correction value D may be defined as:

$$D = W_{prel} - W_{final}$$

where D is the error between the preliminary estimate obtained by the K-model, and the true heating value.

The correction value may be determined based on the flourescence measurements, e.g. as:

$$D = a_2*xrf1 + b_2*xrf2 + c_2*xrf3 + \ldots + z_2*xrfn$$

where xrf1-xrfn are integrated energy counts obtained at certain energy leves and/or energy bands over the fluorescence spectrum. The coefficients, denominated $a_2$-$z_2$ above, are determined and optimized mathematically to provide a correlation between the reference measurements and the heat energy as estimated based on the fluorescence measurements. The coefficients may be determined with a suitable algorithm, such as least squares, partial least squares, or similar methods.

A final estimate of the heating value may then be calculated as:

$$W_{final} = W_{prel} D = a_1*K1 + b_1*K2 + c_1*K3 + \ldots \\ -(a_2*xrf1 + b_2*xrf2 + c_2*xrf3 + \ldots + z_2*xrfn)$$

Figure 3:
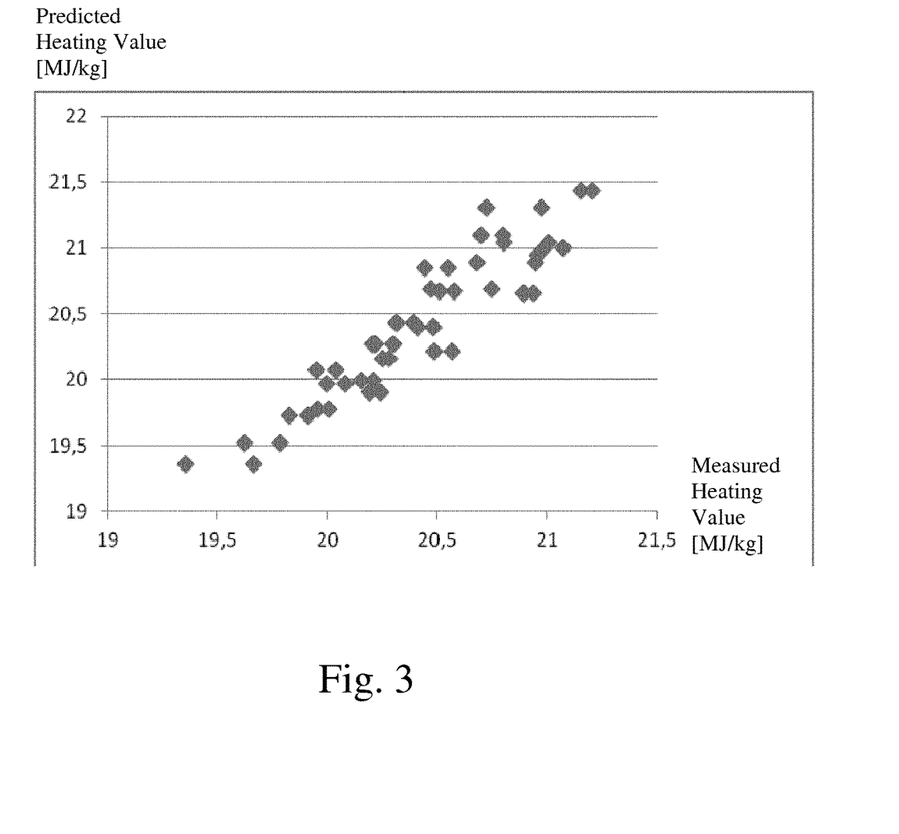
FIG. 3 is a graph showing the correlation between heating values estimated based on the method of the present invention, and heating values measured in an adiabatic bomb calorimeter, for a number of different biological materials.

It has been found by the present inventors that a good approximation of the heating values, and a good correlation between the reference measurements and the estimation based on the transmission and fluorescence measurements, can be achieved. In FIG. 3, a graph is provided showing heating values estimated based on the above-discussed method on one axis, and heating values measured by reference measurements in an adiabatic bomb calorimeter on the other axis, for a number of different biological materials. Radiation having two different energy levels were used, in accordance with the previous discussion, and the content of non-combustible material in the samples varied significantly.

As can be determined from FIG. 3, the estimates of the heating values are a very good approximation of the real heating value, which enables fast, accurate and cost-efficient estimation of the heating values, which can e.g. be used in continuous in-line measurements and similar.

The estimated heating values may be used by the control unit 108, or by other control units, to control e.g. a burning or combustion process effectively.

Figure 2A:
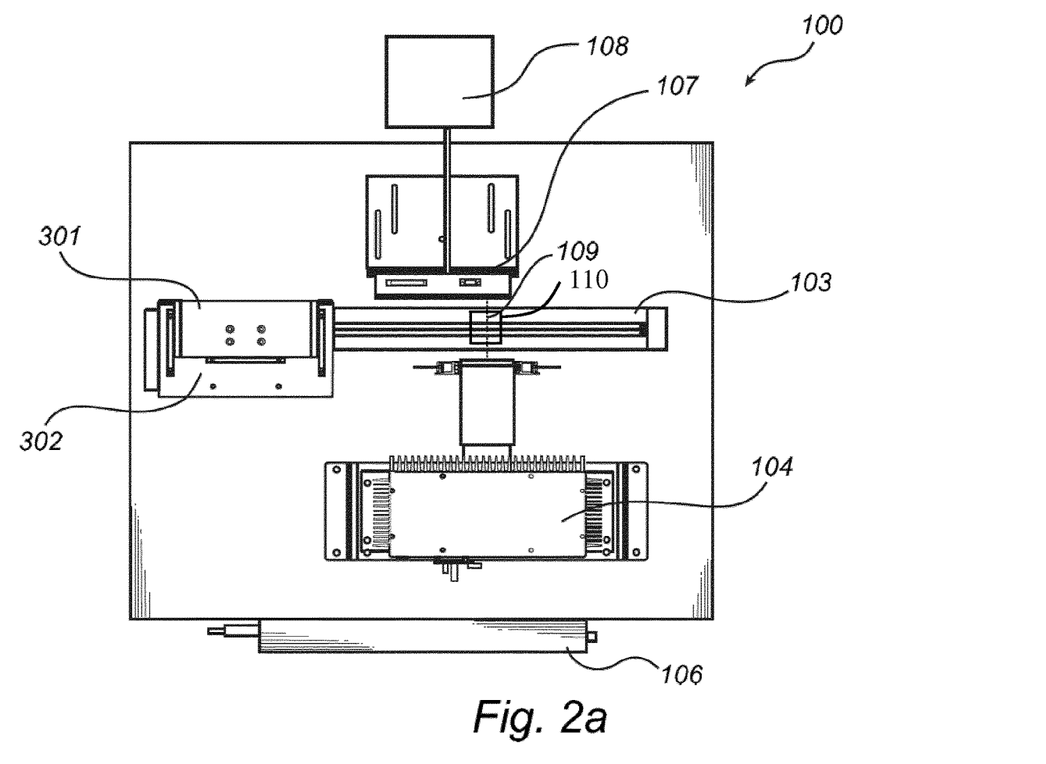
FIG. 2a is a schematic top view of the measurement apparatus.
Figure 2B:
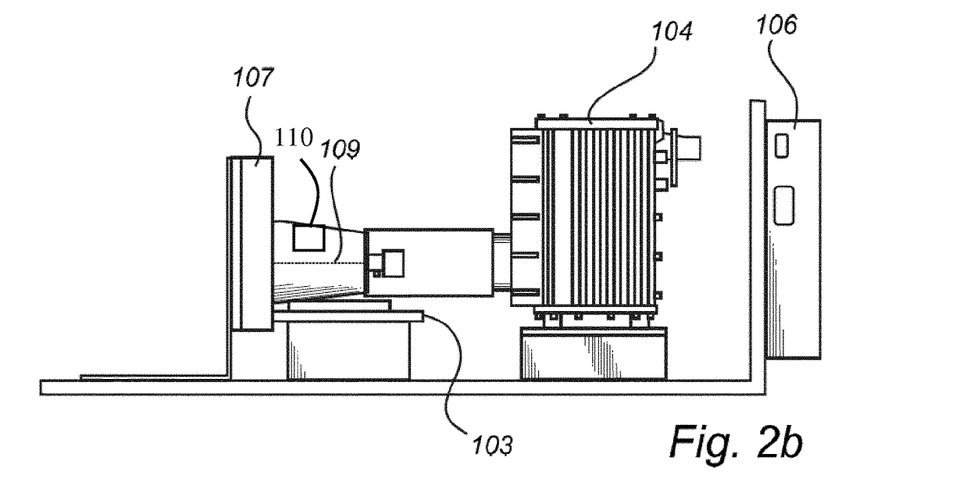
FIG. 2b is a simplified side view of the apparatus of FIG. 2a, where some of the components of the apparatus as shown in FIG. 2a have been excluded for increased clarity.

FIG. 2a-b schematically illustrates an alternative embodiment of a measurement device according the invention. The measurement device 100 comprises a radiation source 104 for irradiating a target area with at least two energy levels/wavelengths. Preferably, the radiation source is an X-ray tube for provision of X-ray radiation of two or more different energies. Preferably, the X-ray tube operates in the range 20-150 kVp. The output radiation from the radiation source is preferably directed towards a target area through a collimator. The radiation source is controlled by means of a controller 106. A transmission detector 107 is arranged on the opposite side of the target area. Further a fluorescence detector 110 is provided. The fluorescence detector 110 is preferably situated where it can have a free line of sight to the material which is measured and which is illuminated with the x-ray source e.g. at some angle beside the x-ray source. A suitable location for the fluorescence detector 110 is illustrated schematically in FIGS. 2a-b, but other positions are also feasible.

The detectors are connected to a control unit 108 that receives detection data from the detector. In this embodiment, the material to be measured is arranged in a sample container 301. The sample container is then arranged on a carrier 302, which is movable in such a way that the sample container is moved through the target area, and thus through the radiation path 109. The carrier may e.g. be moved by means of a conveyor 103. However, other means for moving the carrier are also feasible, such as linear motors, screw arrangements, rail arrangements and the like.

During operation, the sample container is moved through the target area such that preferably all of the material in the sample container is scanned. At the first passage, the material sample is irradiated with radiation of a first energy, and in the second passage, during the return movement, with radiation of a second energy. In order to get a reference value for calibration, it is preferred to measure a calibration material, preferably a predetermined amount of aluminum, at the beginning and end of the passage of the sample container.

Based on these calibration measurements, calibration reference values may be determined in the same way as discussed above, and further, K-value correction values and heating values for the biological material may be calculated as discussed above.

Specific embodiments of the invention have now been described. However, several alternatives are possible, as would be apparent for someone skilled in the art. For example, the number of detectors and/or detector areas may be varied, and the detectors may be arranged at different positions relative the biological sample.

Further, the radiation paths through the material may be arranged in various ways. For example, the paths may travel essentially along a single line, between a radiation source and a detector, or several detectors arranged overlapping or close to each other. However, the radiation paths may also be arranged along parallel lines, to form a "curtain" like measurement zone. It is also possible to use a plurality of non-parallel paths, e.g. extending from a single radiation source to a plurality of spread out detectors, to form a "fan shaped" measurement zone. Similarly, it would also be possible to use a plurality of separated radiation emerging points, and a single detection point, or the like. Many other types of geometries for the paths are also feasible.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed:

1. A method for estimating a heating value of a biological material, comprising:
   irradiating the biological material with X-ray radiation of at least two different energy levels;
   measuring an amount of X-ray radiation transmitted through said biological material at said at least two different energy levels;
   measuring fluorescent X-ray radiation emitted by the biological material when irradiated at said at least two different energy levels; and
   determining a final estimate of the heating value of said biological material, based on a preliminary estimate of the heating value of said biological material, wherein said preliminary estimate is based on said measured transmitted X-ray radiation, and a correction value, based on said measured fluorescent X-ray radiation.

2. The method of claim 1, wherein the preliminary estimate of the heating value is based on said measured transmitted X-ray radiation in correlation with correlation values obtained by X-ray radiation transmitted through a number of different reference materials with known heating values.

3. The method of claim 1, wherein the fluorescent X-ray radiation is used to determine the amount of at least one element having an atomic number greater than 10 in the biological sample, and to determine a correction value based on the determined amount of the at least one element.

4. The method of claim 1, wherein the determination of the final estimated heating value comprises the step of subtracting the correlation value from the preliminary estimate of the heating value or adding the correlation value to the preliminary estimate of the heating value.

5. The method of claim 1, wherein the correction value is determined by estimation of a spectrum integration over at least one energy band of the spectrum of the fluorescent X-ray radiation emitted by the biological material.

6. The method of claim 5, wherein the spectrum integration is made in at least one energy band comprising at least one of: 1.5-10 keV and 25- 90 keV.

7. The method of claim 5, wherein the spectrum integration is made over at least one energy corresponding to a spectrum peak characteristic of at least one of a heavy metal, calcium, potassium, silicon, magnesium and phosphorus.

8. The method of claim 7, wherein the correction value is estimated as an addition of weighted spectrum integrations over specific energies or bands of energies of the fluorescence spectrum.

9. The method of claim 5, wherein the spectrum integration is correlated to a corresponding reduction in heating value by means of measurements of known reference materials.

10. The method of claim 2, wherein the determination of the preliminary estimate of the heating value comprises the steps of:
    determining a quotient between transmission estimates based on said transmission values of two of said at least two energy levels, for each combination of said at least two energy levels;
    multiplying each quotient with a coefficient for each quotient; and
    adding said quotients multiplied by said coefficients,
    wherein said coefficients are determined by said correlation.

11. The method of claim 10, wherein the transmission estimates in said quotients between transmission elements are logarithmic quotients of a calibrated reference value for the transmission at the energy level and the measured transmission values through the biological material at the same energy level.

12. The method of claim 11, wherein the quotients between said transmission estimates are K-values, said K-values being calculated as:

$$K_{AB} = \frac{\ln(N_{0A}/N_A)}{\ln(N_{0B}/N_B)}$$

wherein N0A, N0B are the calibrated reference values for the transmission at the two energy levels A and B, and NA, NB are the transmission values through the biological material at said energy levels.

13. The method of claim 1, wherein the biological material is transported on a conveyor line, and wherein the biological material is irradiated with X-ray radiation, of at least two different energy levels, in a plane substantially perpendicular to a direction of advancement of said conveyor line.

14. The method of claim 1, wherein the X-ray radiation of both said energy levels are emitted from a single X-ray radiation source operating in the energy range of 20-150 kVp.

15. An apparatus for estimating a heating value of a biological material, comprising:
    an X-ray radiation source for irradiation of a biological material with X-ray radiation of at least two different energy levels;

a detector for receiving X-ray radiation transmitted through said biological material, said detector determining, for each energy level, the amount of X-ray radiation transmitted through the biological material;

a fluorescence detector for measuring fluorescent X-ray radiation emitted by the biological material when irradiated at said at least two different energy levels; and a controller arranged to determine a final estimate of the heating value of said biological material based on a preliminary estimate of the heating value of said biological material, wherein said preliminary estimate is based on said measured transmitted X-ray radiation, and a correction value, based on said measured fluorescent X-ray radiation.

16. A method for estimating a heating value of a biological material, comprising:

irradiating the biological material with X-ray radiation of at least two different energy levels;

measuring an amount of X-ray radiation transmitted through said biological material at said at least two different energy levels;

measuring fluorescent X-ray radiation emitted by the biological material when irradiated at said at least two different energy levels; and determining a final estimate of the heating value of said biological material, based on a preliminary estimate of the heating value of said biological material, wherein said preliminary estimate is based on said measured transmitted X-ray radiation, and a correction value, based on said measured fluorescent X-ray radiation, wherein the determination of the final estimated heating value comprises the step of subtracting the correlation value from the preliminary estimate of the heating value or adding the correlation value to the preliminary estimate of the heating value.

17. An apparatus for estimating a heating value of a biological material, comprising:

an X-ray radiation source for X-ray irradiation of a biological material with X-ray radiation of at least two different energy levels;

a detector for receiving X-ray radiation transmitted through said biological material, said detector determining, for each energy level, the amount of X-ray radiation transmitted through the biological material;

a fluorescence detector for measuring fluorescent X-ray radiation emitted by the biological material when irradiated at said at least two different energy levels; and a controller arranged to determine a final estimate of the heating value of said biological material based on a preliminary estimate of the heating value of said biological material, wherein said preliminary estimate is based on said measured transmitted X-ray radiation, and a correction value, based on said measured fluorescent X-ray radiation, wherein the determination of the final estimated heating value comprises the step of subtracting the correlation value from the preliminary estimate of the heating value or adding the correlation value to the preliminary estimate of the heating value.

18. The method of claim 5, wherein the spectrum integration is made in an energy band of 1.5-10 keV.

19. The method of claim 5, wherein the spectrum integration is made in an energy band of 25- 90 keV.

* * * * *